(12) United States Patent
Nash et al.

(10) Patent No.: US 12,065,798 B1
(45) Date of Patent: Aug. 20, 2024

(54) SYSTEM AND METHOD FOR PRE-EMPTIVE PROPERTY SHIFTING DETECTION AND REMEDIATION

(71) Applicant: United Services Automobile Association (USAA), San Antonio, TX (US)

(72) Inventors: Justin Royell Nash, Little Elm, TX (US); Gregory David Hansen, San Antonio, TX (US); Nathan Lee Post, Rockport, TX (US); Jose L. Romero, Jr., San Antonio, TX (US); Andre Rene Buentello, San Antonio, TX (US); Brian Francisco Shipley, Plano, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 141 days.

(21) Appl. No.: 17/678,731

(22) Filed: Feb. 23, 2022

Related U.S. Application Data

(60) Provisional application No. 63/153,026, filed on Feb. 24, 2021.

(51) Int. Cl.
| | | |
|---|---|---|
| *G08B 21/00* | (2006.01) | |
| *E02D 31/10* | (2006.01) | |
| *E02D 33/00* | (2006.01) | |
| *G01C 5/00* | (2006.01) | |
| *G01C 9/00* | (2006.01) | |
| *G01N 33/24* | (2006.01) | |
| *G06Q 40/08* | (2012.01) | |

(52) U.S. Cl.
CPC ............. *E02D 33/00* (2013.01); *E02D 31/10* (2013.01); *G01C 5/00* (2013.01); *G01C 9/00* (2013.01); *G01N 33/246* (2013.01); *G06Q 40/08* (2013.01); *E02D 2600/10* (2013.01)

(58) Field of Classification Search
CPC ..... E02D 33/00; E02D 31/10; E02D 2600/10; G01C 5/00; G01C 9/00; G01N 33/246; G06Q 40/08
USPC ....................................................... 340/689
See application file for complete search history.

(56) References Cited

U.S. PATENT DOCUMENTS

| | | | |
|---|---|---|---|
| 6,282,362 B1 * | 8/2001 | Murphy | H04N 5/9201 |
| | | | 358/909.1 |
| 10,331,092 B1 * | 6/2019 | Billman | G05B 13/028 |
| 2010/0201378 A1 * | 8/2010 | Costanzo | G01M 5/0091 |
| | | | 324/636 |

(Continued)

*Primary Examiner* — Tai T Nguyen
(74) *Attorney, Agent, or Firm* — Fletcher Yoder, P.C.

(57) ABSTRACT

A system for monitoring shifting of a structure includes one or more hardware processors. The system also includes a non-transitory memory, the non-transitory memory storing instructions that, when executed by the one or hardware processors, causes the one or more hardware processors to perform actions. The actions include monitoring the structure for a shift in elevation in a portion of the structure. The actions also include receiving, from a first plurality of sensors, feedback related to a condition of a foundation of a structure. The actions further include determining whether a portion of the foundation of the structure has shifted in elevation based on the feedback. The actions still further include providing a notification when the portion of the structure has shifted in elevation.

17 Claims, 2 Drawing Sheets

(56) References Cited

U.S. PATENT DOCUMENTS

2019/0338487 A1* 11/2019 Niezrecki ............. E02D 27/425

* cited by examiner

SYSTEM AND METHOD FOR PRE-EMPTIVE PROPERTY SHIFTING DETECTION AND REMEDIATION

CROSS-REFERENCE TO RELATED APPLICATION

This application claims priority to and the benefit of U.S. Provisional Patent Application No. 63/153,026, entitled "SYSTEM AND METHOD FOR PRE-EMPTIVE PROPERTY SHIFTING DETECTION AND REMEDIATION", filed Feb. 24, 2021, which is herein incorporated by reference in its entirety.

BACKGROUND

This section is intended to introduce the reader to various aspects of art that may be related to various aspects of the present disclosure, which are described and/or claimed below. This discussion is believed to help provide the reader with background information to facilitate a better understanding of the various aspects of the present disclosure. Accordingly, it is understood that these statements are to be read in this light, and not as admissions of prior art.

Typically, structures such as buildings or homes will shift or settle some over time. In addition, in response to certain weather events (e.g., severe storms) some shifting may also occur (e.g., due to alterations in the conditions of the soil the structure is disposed upon). However, too much shifting or settling may result in damage to the structure and costly repairs. Accordingly, there is a need to detect any shift or settling and to potentially take remedial actions.

SUMMARY

A summary of certain embodiments disclosed herein is set forth below. It should be understood that these aspects are presented merely to provide the reader with a brief summary of these certain embodiments and that these aspects are not intended to limit the scope of this disclosure. Indeed, this disclosure may encompass a variety of aspects that may not be set forth below.

In one embodiment, a system for monitoring shifting of a structure is provided. The system includes one or more hardware processors. The system also includes a non-transitory memory, the non-transitory memory storing instructions that, when executed by the one or hardware processors, causes the one or more hardware processors to perform actions. The actions include monitoring a structure for a shift in elevation in a portion of the structure. The actions also include receiving, from a first plurality of sensors, feedback related to a condition of a foundation of a structure. The actions further include determining whether a portion of the foundation of the structure has shifted in elevation based on the feedback. The actions still further include providing a notification when the portion of the structure has shifted in elevation.

In one embodiment, a system for monitoring shifting of a structure is provided. The system includes a first plurality of sensors configured to be disposed throughout the structure and to measure a condition of a foundation of the structure. The system also includes a second plurality of sensors configured to be disposed in soil along a perimeter of the structure and to measure a condition of the soil. The system further includes an irrigation system configured to be disposed in the soil along the perimeter of the structure. The system still further includes a controller configured to receive feedback from the first and second plurality of sensors and to determine based on the feedback whether a portion of the foundation of the structure has shifted in elevation and to activate the irrigation system, based on a detected shift in the elevation, to irrigate a specific portion of the soil to keep the foundation of the structure from shifting in elevation.

In one embodiment, a computer-implemented method for monitoring shifting of a structure is provided. The method includes monitoring, via a processor, the structure for a shift in elevation in a portion of the structure. The method also includes receiving, at the processor, feedback related to a condition of a foundation of a structure from a plurality of sensors. The method further includes determining, via the processor, whether a portion of the foundation of the structure has shifted in elevation based on the feedback. The method still further includes providing, via the processor, a notification when the portion of the structure has shifted in elevation. The method yet further includes monitoring, via the processor, one or more actions taken in response to the notification and adjusting insurance characteristics based on the one or more actions.

BRIEF DESCRIPTION OF THE DRAWINGS

These and other features, aspects, and advantages of the disclosed subject matter will become better understood when the following detailed description is read with reference to the accompanying drawings in which like characters represent like parts throughout the drawings, wherein.

DETAILED DESCRIPTION

Figure 1:
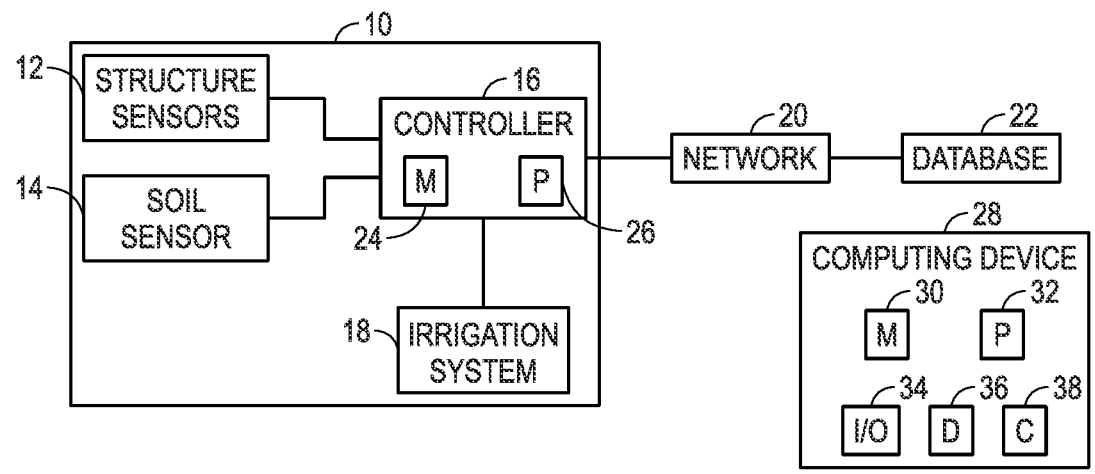
FIG. 1 illustrates a block diagram of a system for detecting shifting in a structure (e.g., building or home), in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

When introducing elements of various embodiments of the present disclosure, the articles "a," "an," and "the" are intended to mean that there are one or more of the elements. The terms "comprising," "including," and "having" are intended to be inclusive and mean that there may be additional elements other than the listed elements. Additionally, it should be understood that references to "one embodiment," "an exemplary embodiment," or "an embodiment" of the present disclosure are not intended to be interpreted as excluding the existence of additional embodiments that also incorporate the recited features.

As may be appreciated, implementations of the present disclosure may be embodied as a system, method, device, or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present disclosure may take the form of a computer program product embodied in one or more computer readable medium(s) having computer-readable program code embodied thereon.

The present embodiments provide systems and methods for detecting shifting in a structure (e.g., building or home). In particular, sensors may be disposed at various locations throughout a structure to monitor a condition of the structure (e.g., a shift in elevation or a change in angle of the structure or a foundation of the structure). In addition, sensors may be disposed on or in the soil about the perimeter of the structure to monitor conditions in the soil (moisture level, density, etc.). A controller based on the feedback from the sensors disposed throughout the structure can monitor for elevation shifts or angle changes in a portion of the structure. In addition, the controller, based on the feedback from the sensors disposed on or in the soil, may determine a potential cause of any elevation shift in the structure due to the condition of the soil or activate an irrigation system to alter the condition of the soil to mitigate the elevation shift or to pre-emptively keep the elevation shift from occurring. In some embodiments, the controller may provide a notice to a person associated with the structure (e.g., owner, occupant, etc.) of the condition of the structure and/or soil, potential causes of a condition in the structure, potential remediation suggestions or recommendations, or actions (proactive or remedial) taken by the controller. The disclosed systems and methods may mitigate or avoid significant shifts in elevation in the structure and avoid potential damage and costly repairs.

FIG. 1 illustrates a block diagram of a system 10 for detecting shifting in a structure (e.g., building or home). The system includes a controller 12, sensors (e.g., structure sensors) 14, sensors (e.g., soil sensors) 16, and an irrigation system 18. The sensors 14 are disposed at a variety of locations (e.g., strategic locations) throughout the structure (e.g., building or home). For example, if a home had four corners, at least one sensor 14 may be disposed in each corner. The number of structure sensors 14 may vary (e.g., 2, 3, or more). The structures sensors 14 may include one or more pressure sensors (e.g., strain gauges, pressure altimeter (e.g., pressurized hydrostatic altimeter), barometer (e.g., aneroid barometer), piezoelectric, etc.) that can be utilized to reference the elevation of a portion the structure (e.g., a portion of the foundation) relative to a set elevation (e.g., initial elevation when the sensor is installed). In other embodiments, the structure sensors 14 may include one or more tilt sensors (e.g., force balance sensor, solid state micro-electromechanical systems, fluid-filled sensors, accelerometers, etc.) that can be utilized to determine a tilt or change in angle of the structure relative to an initial point or reference point (e.g., level condition). Upon installation of the structure sensors 14, the sensors 14 may be calibrated (e.g., relative to a reference such as a reference elevation or tilt condition (e.g., level condition). The sensors 14 may provide feedback related to a condition (e.g., change in elevation or angle) of a portion of the structure.

The sensors 16 may be disposed on or within the soil adjacent and along a perimeter of the structure. The number of the sensors 16 (e.g., soil sensors) may vary (e.g., 2, 3, or more). The sensors 16 may include one or more moisture sensors (tensiometric sensors, volumetric sensors, or time domain reflectometry devices, etc.) to measure a moisture level within the soil. The sensors 16 may include one or more solid state sensors (e.g., gypsum blocks, granular matrix sensors, etc.) to measure soil water tension. The sensors 16 may include soil strength sensors (e.g., penetrometer, etc.) to measure a density or compactness of the soil. The sensors 16 may provide feedback related to a condition (e.g., moisture level, water tension level, density or compactness, etc.) of the soil adjacent the perimeter of the structure.

The irrigation system 18 may include one or more soaker hoses disposed on or in the soil adjacent to and along the perimeter of the structure. In certain embodiments, the irrigation system 18 may include a sprinkler system. The irrigation system 18 may be utilized to water portions of the soil adjacent the perimeter of the structure. In certain embodiments, a water reservoir or catch system (e.g., to collect free water (e.g., rain) for future use) may be utilized in conjunction with the irrigation system 18 during times of water restriction. In certain embodiments, the irrigation system 18 may be coupled to the water reservoir or catch system 19 so that the water reservoir or catch system 19 may provide water to the irrigation system 18 in times of drought, drought restrictions, and/or water restrictions.

The structure sensors 12, the soil sensors 14, and the irrigation system 18 are in communication with the controller 16. In addition, the controller 16 may be communicatively coupled to one or more databases 22 (e.g., weather database) via any suitable communication network or networks 20, including a mobile communication network, a Wi-Fi network, local area network (LAN), wide area network (WAN), and/or the Internet. The database 22 (e.g., weather database) may provide weather information (past, current, future, etc.) for the location of the structure, which controller 16 may associate with a change in condition of a structure or soil. For example, the controller 16 may determine based on the information from the databases 22 that drought conditions are present or that drought restrictions and/or water restrictions are currently being implemented, which may enable the controller 18 to utilize the water reservoir or catch system 19 in conjunction with the irrigation system.

The controller 16 includes a memory 24 and a processor 26. The processor 26 may be any type of computer processor or microprocessor capable of executing computer-executable code. The processes and logic flows described in this specification may be performed by one or more programmable processors executing one or more computer programs to perform functions by operating on input data and generating output. The processes and logic flows may also be performed by special purpose logic circuitry, e.g., an FPGA (field programmable gate array) or an ASIC (application specific integrated circuit). Processors suitable for the execution of a computer program include, by way of example, both general and special purpose microprocessors, and/or processor(s) of any appropriate kind of digital computer.

The memory 24 may be any suitable articles of manufacture that store processor-executable code, data, or the like.

These articles of manufacture may include non-transitory computer-readable media (e.g., any suitable form of memory or storage) that may store the processor-executable code used by the processor 26 to perform the presently disclosed techniques. It should be noted that non-transitory merely indicates that the media is tangible and not a signal.

The controller 16 may receive feedback from the structure sensors 12 and determine whether a portion of the structure (e.g., portion of the foundation of the structure) has shifted in elevation (e.g., up or down) or changed an angle (relative to either an initial or reference elevation or angle). The controller 16 may also receive feedback from the soil sensors 16 to determine a condition of the soil (e.g., moisture level, density or compactness, etc.). The controller 16 may compare the feedback from the sensors 12, 14 to thresholds (e.g., reference states for elevation or angles or desired moisture level for a soil, etc.). The controller 16 may also store the data collected from the sensors 12, 14 in the memory 24 or other storage for later reference.

In response to any change in elevation or angle of a portion of the structure, the controller 16 may ascertain a potential cause (e.g., soil condition, weather event, etc.) and/or provide a recommendation or suggestion for remediation (e.g., water a certain portion of the soil, add soil in a certain area, etc.). In certain embodiments, the controller 16 may take action in response to the change in elevation or angle of the portion of the structure. For example, the controller 16 may send a control signal to the irrigation system 18 to water a certain portion of the soil (e.g., to a certain moisture level). In certain embodiments, the controller 16 may take pre-emptive action before any change in condition of the structure is detected. For example, based on a condition of the soil, the controller 16 may send a control signal to the irrigation system 18 to water a certain portion of the soil (e.g., to a certain moisture level). The controller 16 may also take into account a weather forecast in controlling the moisture level of the soil via the irrigation system 18. In certain embodiments, the controller 6 may send a control signal to the irrigation system 18 and/or the water reservoir or catch system 19 to utilize the water reservoir or catch system 19 as the water supply for irrigation (e.g., in the presence of water restrictions or a drought condition).

The controller 16 may be in communication with one or more computing device 28 (e.g., a user device). The computing device may include a memory 30 (e.g., similar to memory 24), a processor 32 (e.g., similar to processor 26), input/output (I/O) port 34 (e.g., mouse, keyboard, touchscreen, stylus, etc.), a display 36, and a communication component 38 (e.g., to enable communication with the controller 16). The memory 30 may store an application for interacting with the controller 16 for the system 10. As used herein, applications may include any suitable computer software or program that may be installed onto the computing device 28 and executed by the processor 32. The display 36 may enable the display of any data acquired by the controller 16 (e.g., via the sensors 12, 14), any notification or alerts related to a condition of the structure, any recommendations related to a change in the structure or to pre-emptively avoid any change in the structure, or a notice of any action in response to a change in the structure or pre-emptive action taken by the controller 16. In addition, the computing device 28 may enable any commands or information to be provided to the controller 16 (and the system 10). For example, the computing device 28 may enable a user to input instruction regarding irrigation of one or more areas of the soil about the structure.

Figure 2:
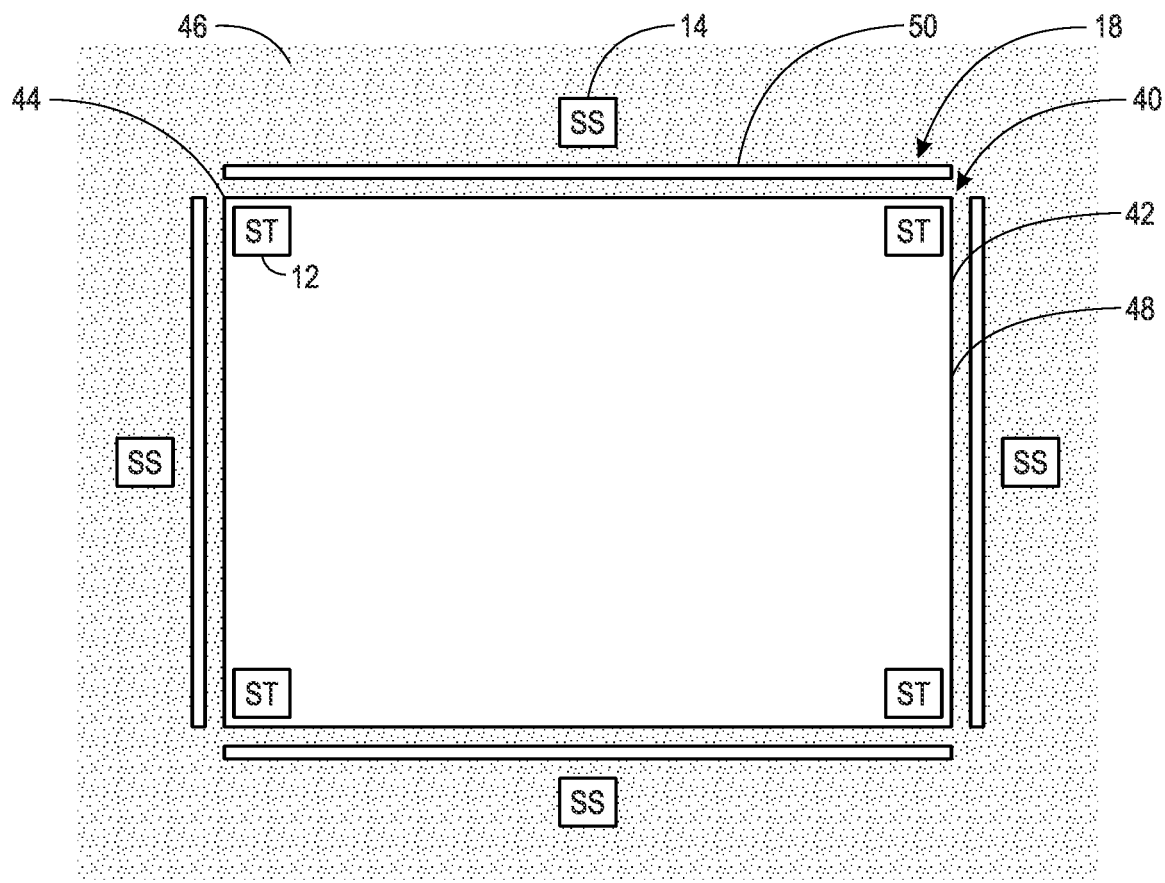
FIG. 2 illustrates a schematic diagram for sensor placement and irrigation system placement relative to a structure, in accordance with embodiments described herein.

FIG. 2 illustrates a schematic diagram of sensor placement and irrigation system placement relative to a structure 40 (e.g., home or building). An outline of the structure 40 (e.g., in plan view) is indicated by a perimeter 42. One or more structure sensors 12 (ST), as described above, may be located throughout the structure 40. The structure sensors 12 are distributed throughout the structure 40 to provide an indication of a change in condition (e.g., elevation or angle) of any portion of the structure 40. As depicted, the structure sensors 12 are distributed in each corner 44 of the structure 40. The structure sensors 12 may be located in other locations (e.g., centrally located, located in the area between corners 44, etc.). The structure sensors 12 may be associated with the foundation or floor or wall or other portion of the structure 40. The structure sensors 12 may be located internally within the structure 40 and/or externally on the structure 40.

One or more soil sensors 14 (SS), as described above, may be disposed in or on soil 46 disposed adjacent to and about the perimeter 42 of the structure 40. As depicted, at least one soil sensor 14 is disposed on the soil 46 on each side 48 of the structure 40. The soil sensors 14 are distributed throughout the soil 46 to provide an indication of a change (e.g., in moisture level, compactness, etc.) in the soil 46 near the structure 40.

The irrigation system 18 is disposed on or in the soil 46 about the perimeter 42 of the structure 40. In certain embodiments, the irrigation system 18 includes one or more soaker hoses 50. The number of soaker hoses 50 may vary. A length of each soaker hose 50 may vary. As depicted, one soaker hose 50 is located on each side 48 of the structure 40. In certain embodiments, more than one soaker hose 50 may be located on each side 48 of the structure 40. In certain embodiments, a particular soaker hose 50 may extend from one side of the structure 40 to another side 48 of the structure 40 (i.e., around the corner 44). In certain embodiments, the irrigation system 18 may include a sprinkler system. The zones of the sprinkler system disposed adjacent to and about the perimeter 42 may be utilized to manage the moisture of the soil 46 to avoid any change in the condition of the structure 40.

Figure 3:
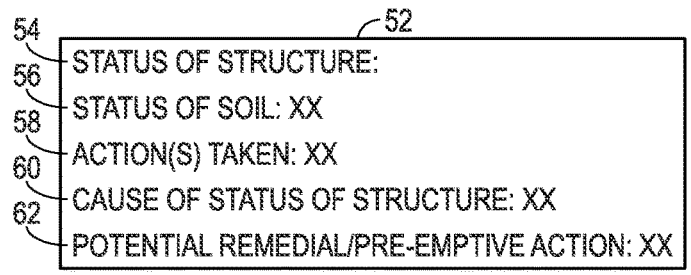
FIG. 3 is an illustration of a graphical user interface displaying, on a computing device, information related to a condition of a structure, in accordance with embodiments described herein.

FIG. 3 is an illustration of a graphical user interface 52 displaying, on a computing device (e.g., computing device 28 in FIG. 1), information related to a condition of a structure. As depicted, the graphical user interface 52 may display a status of the structure indicator 54 provided by the controller (e.g., controller 16 in FIG. 1). The indicator 54 may indicate a change in a condition of a portion of the structure (e.g., shift in elevation and/or change in angle). Some examples of what the indicator 54 may state are "No change throughout structure", "Change in elevation in back left room", and "Change in angle in front right corner of structure". In certain embodiment, the indicator 54 may provide a measurement as well. For example, the indicator 55 may state "Change of negative 0.1 centimeters in elevation in back left room" or "Change in of negative 1 degree in front right corner of structure".

The graphical user interface 52 may also display a status soil indicator 56 provided by the controller. The indicator 56 may indicate a current condition and/or a change in the condition of one or more areas of the soil disposed about a perimeter of the structure. Some examples of what the indicator 56 may state are "No change in the soil", "Soil near back right corner of structure is in need of moisture", and "Soil near front left corner has become less compact or dense". In certain embodiments, the indicator 56 may provide a measurement related to the condition of the soil at one or more areas of the soil relative to the structure. For example, "Soil located adjacent to back right corner of structure has a moisture level of X" or "Soil located adjacent to left right corner has a density or compactness of X".

The graphical user interface 52 may further display an action(s) taken indicator 58. The indicator 58 may provide an indication of a remedial action (preemptive or in response to a change in the condition of the structure or soil) taken by the controller. For example, the indicator 58 may state "Soil adjacent left rear corner of structure was irrigated", "Soil adjacent right rear corner of structure was irrigated with 0.1 inches of water", or "Watering of the soil has been delayed for 3 days due to anticipated precipitation today". Monitoring of such actions may be utilized by a system (e.g., computing device 28) to adjust insurance premiums or other aspects of an insurance product, which can also be presented for review via the graphical user interface 52. For example, consistent remedial action taken over time in response to detected structural issues may result in a lowering or maintaining of certain insurance characteristics (e.g., premium levels) while a lack of action may result in an increase in such characteristics. Other changes to insurance are contemplated as well in response to whether the changes in structural conditions are addressed by detected actions.

In certain embodiments, the graphical user interface 52 includes a cause of status of the structure indicator 60. If there is a change in the condition of the structure, the indicator 60 may provide the cause. The indicator 60 may state "Storm on July 2 caused a change in soil moisture that may have caused the change in elevation on front right corner of the structure" or "Change in soil density or compactness in soil adjacent the back left corner of the structure may have caused the change in elevation".

In certain embodiments, the graphical user interface 52 includes a potential remedial or preemptive action indicator 62. The indicator 62 may be for any suggestion or recommended action to be taken (as suggested by the controller) in response to a change in condition of the structure and/or soil or to avoid any change in condition of the structure and/or soil. The indicator 62 may state "Add soil to the area adjacent back left corner of the house", "Water the soil adjacent the front right corner of the house", or "Compact the soil in the area adjacent the back left corner of the house".

Figure 4:
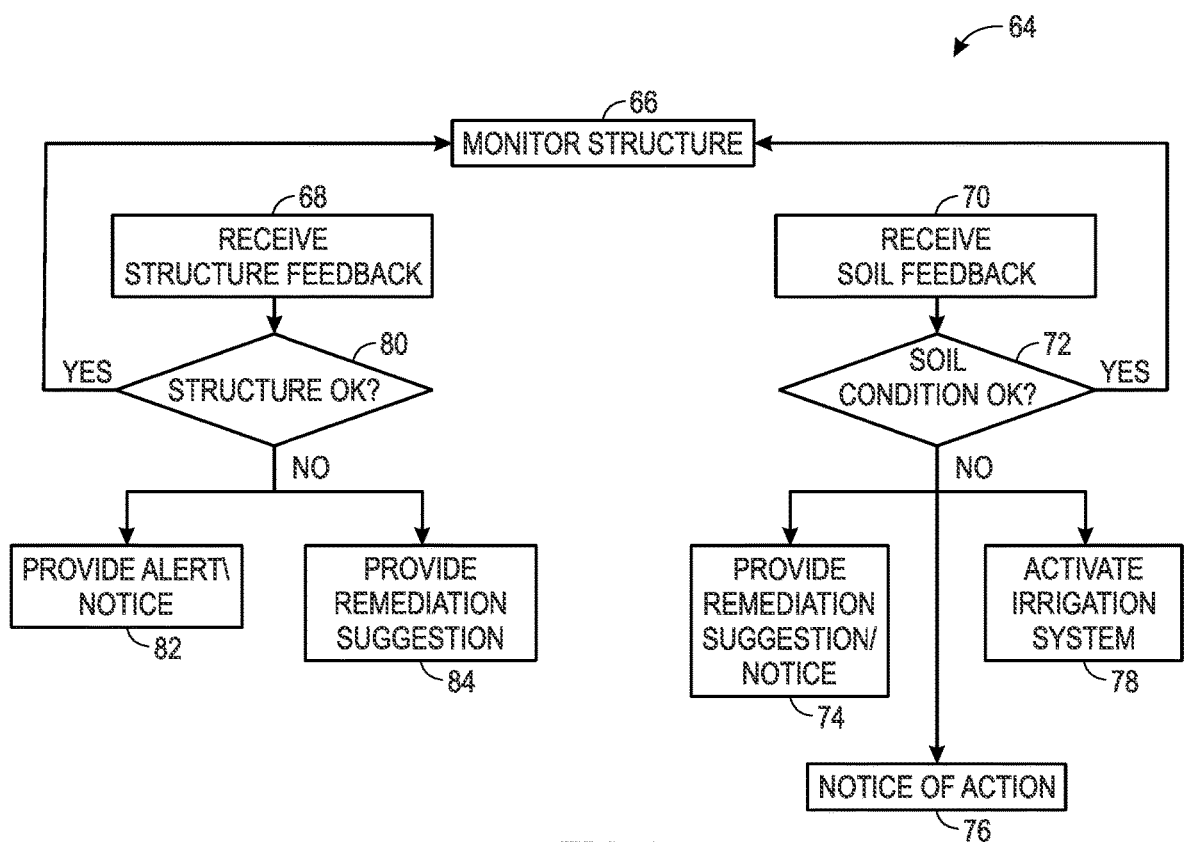
FIG. 4 illustrates a flow diagram of a method for monitoring a condition of a structure, in accordance with embodiments described herein.

FIG. 4 illustrates a flow diagram of a method 64 for monitoring a condition of a structure. One or more steps of the method 64 may be carried out by one or more components of the system illustrated in FIG. 1. One or more of the steps of the method 64 may be performed simultaneously or in a different order from the order depicted in FIG. 4. One or more of the steps 64 of the method 64 may be combined.

The method 64 includes monitoring a structure (e.g., home or building) (block 66). The method 64 includes receiving structure feedback (e.g., from structure sensors as described above) (block 68). The method 66 also includes receiving soil feedback (e.g., from soil sensors as described above) adjacent to and disposed about the structure (block 70).

The method 64 includes determining if one or more soil conditions (e.g., moisture, density or compactness, etc.) are okay based on the feedback from the soil sensors (block 72). In determining if a soil condition is okay, the feedback from the soil sensors may be compared to a set or desired threshold or range to determine if a particular measurement is above or below the threshold or within or without the range. If the soil conditions are okay, the monitoring of the structure continues (block 66). If one or more soil conditions in one or more areas of the soil are not okay, the method 64 includes providing a notice for a recommendation or suggestion to remedy the soil condition (block 74). For example, the notice may state to water a certain area of the soil, to add soil to a certain area, or to compact a certain area of the soil. In certain embodiments, if one or more soil conditions in one or more areas of the soil are not okay, the method 64 includes providing a notice of an action taken by the controller with regards to the soil (block 76). For example, the notice of action may be that the area of the soil adjacent the back right corner of the structure was watered with 0.1 inches of water. In certain embodiments, if one or more soil conditions in one or more areas of the soil are not okay, the method 64 includes automatically activating (in a proactive manner) the irrigation system (block 78) to water one or more areas of the soil that need moisture. As noted above, in certain embodiments, a water reservoir or catch system may be utilized to supply water to the irrigation system.

The method 64 also includes determining if a condition of a structure (e.g., angle or elevation) is okay based on the feedback from the structure sensors (block 80). In determining if the condition of the structure is okay, the feedback from the structure sensors may be compared to a reference (e.g., angle or elevation) to determine if a particular measurement has changed from the reference. If the condition of the structure is okay, the monitoring of the structure continues (block 66). If the condition of one or more areas of the structure is not okay, the method 64 includes providing an alert or notice (block 82). The alert or notice may provide an indication of the condition (e.g., shift in elevation or change in angle of a portion of the structure). In certain embodiments, the alert or notice may provide an indication of the potential cause (e.g., soil condition in a particular area about the structure, a weather event, etc.). In certain embodiments, the alert or notice may also provide an action taken (e.g., watering of area of the soil). In certain embodiments, if the condition of a portion of the structure is not okay, the method 64 includes providing recommendation or suggestion for remediation (e.g., add soil in a certain area, water the soil in a certain area, contact a professional to remedy the condition, etc.) (block 84).

While the embodiments set forth in the present disclosure may be susceptible to various modifications and alternative forms, specific embodiments have been shown by way of example in the drawings and have been described in detail herein. However, it should be understood that the disclosure is not intended to be limited to the particular forms disclosed. The disclosure is to cover all modifications, equivalents, and alternatives falling within the spirit and scope of the disclosure as defined by the following appended claims.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A system for monitoring shifting of a structure, comprising:

a first plurality of sensors configured to be disposed at a plurality of locations throughout the structure;

a second plurality of sensors configured to be located on or within soil adjacent a perimeter of the structure;

one or more hardware processors; and a non-transitory memory, the non-transitory memory storing instructions that, when executed by the one or more hardware processors, causes the one or more hardware processors to perform actions comprising:

monitoring the structure for a shift in elevation in a portion of the structure;

receiving, from the first plurality of sensors, feedback related to a condition of a foundation of the structure;

receiving, from the second plurality of sensors, feedback related to a condition of the soil adjacent the perimeter of the structure;

determining whether a portion of the foundation of the structure has shifted in elevation based on the feedback; and providing a notification when the portion of the structure has shifted in elevation.

2. The system of claim 1, wherein the plurality of locations comprises corners of the structure.

3. The system of claim 1, wherein the first plurality of sensors comprises at least one tilt sensor configured to measure a change in angle of the foundation.

4. The system of claim 1, wherein the first plurality of sensors comprises at least one pressure sensor configured to measure a change in the elevation of the foundation.

5. The system of claim 4, wherein the at least one pressure sensor comprises a hydrostatic altimeter.

6. The system of claim 1, wherein the condition of the foundation of the structure comprises an angle or the elevation of the foundation.

7. The system of claim 1, wherein the instructions, when executed by the one or more hardware processors, causes the one or more hardware processors to perform actions comprising providing a recommendation for remediating the shift in the elevation of the portion of the structure.

8. The system of claim 1, wherein the instructions, when executed by the one or more hardware processors, causes the one or more hardware processors to perform actions comprising providing a potential cause of the shift in the elevation of the portion of the structure.

9. The system of claim 1, wherein the instructions, when executed by the one or more hardware processors, causes the one or more hardware processors to perform actions comprising providing a notification when the condition of the soil is not at an adequate moisture level to maintain the foundation of the structure at a set elevation.

10. The system of claim 1, wherein the second plurality of sensors comprises at least one moisture sensor.

11. The system of claim 1, comprising an irrigation system configured to irrigate the soil adjacent the perimeter of the structure.

12. The system of claim 11, wherein the instructions, when executed by the one or more hardware processors, causes the one or more hardware processors to perform actions comprising providing a signal to the irrigation system that causes the irrigation system to irrigate a specific area of the soil.

13. The system of claim 11, wherein the irrigation system comprises one or more soaker hoses disposed in the soil about the perimeter of the structure.

14. The system of claim 11, wherein the irrigation system comprises a sprinkler system.

15. The system of claim 1, wherein the structure comprises a house.

16. A system for monitoring shifting of a structure, comprising:

a first plurality of sensors configured to be disposed throughout the structure and to measure a condition of a foundation of the structure;

a second plurality of sensors configured to be disposed in soil along a perimeter of the structure and to measure a condition of the soil;

an irrigation system configured to be disposed in the soil along the perimeter of the structure; and a controller configured to receive feedback from the first and second plurality of sensors and to determine, based on the feedback, whether a portion of the foundation of the structure has shifted in elevation and to activate the irrigation system, based on a detected shift in the elevation, to irrigate a specific portion of the soil to keep the foundation of the structure from shifting in elevation.

17. A computer-implemented method for monitoring shifting of a structure, comprising:

monitoring, via a processor, the structure for a shift in elevation in a portion of the structure;

receiving, at the processor, feedback related to a condition of a foundation of the structure from a first plurality of sensors;

receiving, at the processor, feedback related to a condition of the soil adjacent the perimeter of the structure from a second plurality of sensors, wherein the second plurality of sensors is located on or within soil adjacent a perimeter of the structure;

determining, via the processor, whether a portion of the foundation of the structure has shifted in elevation based on the feedback from both the first plurality of sensors and the second plurality of sensors;

providing, via the processor, a notification when the portion of the structure has shifted in elevation; and monitoring, via the processor, one or more actions taken in response to the notification and adjusting insurance characteristics based on the one or more actions.

* * * * *